US009271848B2

(12) United States Patent
Brooks

(10) Patent No.: US 9,271,848 B2
(45) Date of Patent: Mar. 1, 2016

(54) PROSTHETIC JOINT COMPONENT PLANNING TEMPLATE

(75) Inventor: Peter John Brooks, Gates Mills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 705 days.

(21) Appl. No.: 12/603,156

(22) Filed: Oct. 21, 2009

(65) Prior Publication Data

US 2010/0106253 A1    Apr. 29, 2010

Related U.S. Application Data

(60) Provisional application No. 61/108,169, filed on Oct. 24, 2008.

(51) Int. Cl.
  *A61F 2/46*     (2006.01)
  *A61B 19/00*    (2006.01)
  *A61F 2/36*     (2006.01)

(52) U.S. Cl.
  CPC ......... *A61F 2/4657* (2013.01); *A61B 2019/461* (2013.01); *A61F 2/4684* (2013.01); *A61F 2002/3611* (2013.01); *A61F 2002/4658* (2013.01); *A61F 2002/4659* (2013.01)

(58) Field of Classification Search
  CPC .............................. A61F 2/4657; A61F 2/4684
  USPC ........................................ 606/102; 623/23.12
  See application file for complete search history.

(56) References Cited

U.S. PATENT DOCUMENTS

| 4,211,228 | A | * | 7/1980 | Cloutier ........................ 606/102 |
| 4,524,766 | A |   | 6/1985 | Petersen |
| 4,959,066 | A | * | 9/1990 | Dunn et al. ..................... 606/89 |
| 5,342,366 | A |   | 8/1994 | Whiteside et al. |
| 5,423,827 | A |   | 6/1995 | Mumme et al. |
| 5,607,431 | A |   | 3/1997 | Dudasik et al. |
| 5,885,297 | A |   | 3/1999 | Matsen, III |
| 6,258,097 | B1 | * | 7/2001 | Cook et al. ..................... 606/91 |
| 7,273,500 | B2 |   | 9/2007 | Williamson |
| 2004/0122439 | A1 | * | 6/2004 | Dwyer et al. ................ 606/102 |
| 2004/0153091 | A1 |   | 8/2004 | Figueroa et al. |
| 2006/0111726 | A1 |   | 5/2006 | Felt et al. |
| 2007/0191960 | A1 | * | 8/2007 | Evans ........................ 623/22.12 |
| 2008/0221697 | A1 |   | 9/2008 | Graser |

\* cited by examiner

*Primary Examiner* — Bruce E Snow
*Assistant Examiner* — Melissa Hoban
(74) *Attorney, Agent, or Firm* — Tarolli, Sundheim, Covell & Tummino LLP

(57) ABSTRACT

A method for planning the implantation of a prosthetic joint component in a prosthesis-receiving bone is described. Surrounding soft tissue is retracted to expose the prosthesis-receiving bone. A prosthetic joint component planning template comprising a planar template body having a unitary structure is provided. The planning template is positioned in a superimposed orientation with a curvilinear surface of an exposed prosthesis-receiving bone. The position of the planning template is adjusted into a desired superimposed orientation with respect to the prosthesis-receiving bone. At least one of a size and an orientation of the prosthetic joint component is determined through visualization of the planning template and the prosthesis-receiving bone. An apparatus for assisting a user with determining at least one of a size and an orientation of a prosthetic joint component is also provided.

10 Claims, 4 Drawing Sheets

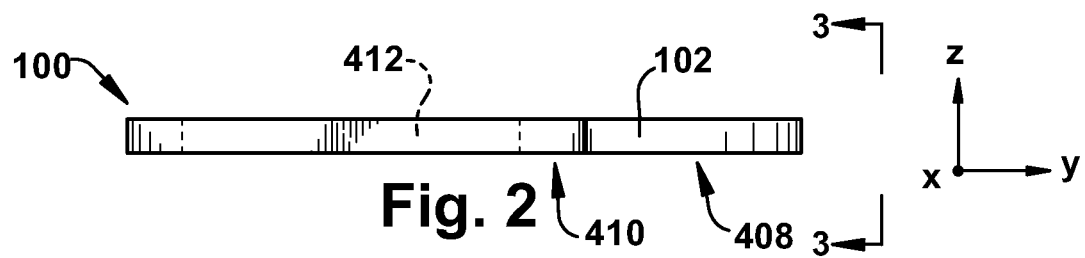
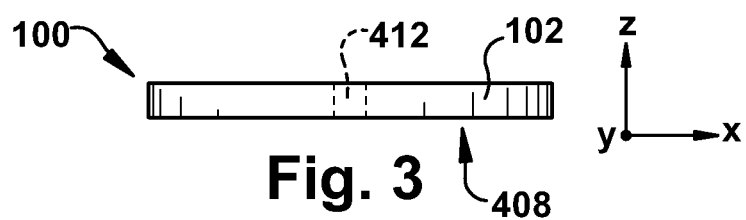
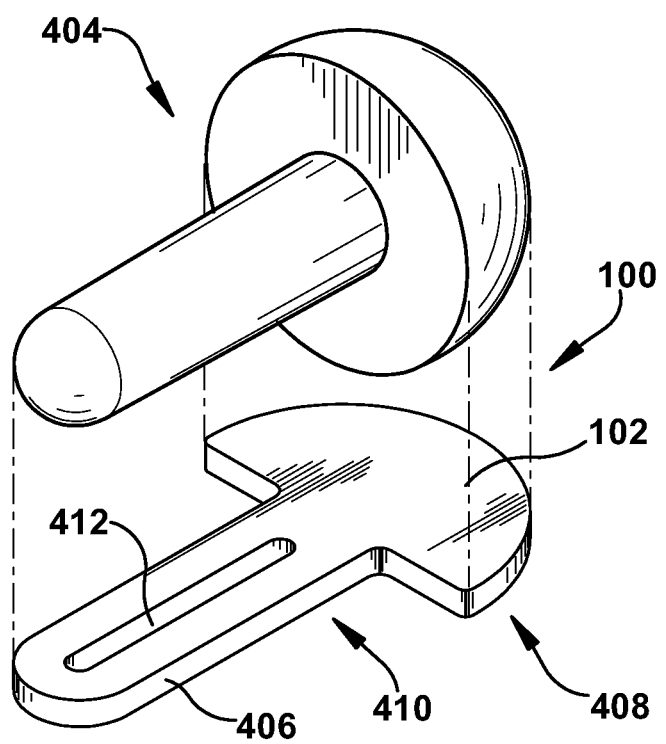

PROSTHETIC JOINT COMPONENT PLANNING TEMPLATE

RELATED APPLICATION

This application claims priority from U.S. Provisional Application No. 61/108,169, filed 24 Oct. 2008, the subject matter of which is incorporated herein by reference.

TECHNICAL FIELD

The present invention relates to an apparatus and method for use of a prosthetic joint component planning template and, more particularly, to a planning template for visually determining at least one of a size and an orientation of a prosthetic joint component.

BACKGROUND OF THE INVENTION

Most recommended techniques for hip resurfacing and/or replacement advise the use of a jig to properly position the implant on the upper femur. Many such jigs are anchored on the femur by a reference pin, carefully placed for correct alignment. This reference pin is placed according to pre-operative planning, either manually using X-rays and plastic overlay templates, or using specialized and expensive computer software and digital patient imaging. Once this reference pin is placed during the surgery, the jig is applied, and the resurfacing or replacement operation proceeds.

A common method for reference pin placement includes placing a 115% magnified plastic overlay template over a film X-ray and adjusting the overlay template to the desired final position of the implant. 115% was chosen because a patient of average build, X-rayed in a standard manner, often appears to have been magnified to that scale on the developed X-ray film. A 115% scaled ruler on the overlay template is then used to measure the distance from the desired reference pin location to a bony landmark on the X-ray. During surgery, a regular ruler may then be used to space the corresponding reference pin location from the bony landmark on the patient's bone, and the reference pin is drilled into place.

Unfortunately, incorrect placement of the reference pin may result from inaccuracies in the recommended methods, and these errors can have deleterious effects on the outcome of the procedure. For example, there may be differences in magnification between the X-rays and the overlay templates, leading to improper placement when measurements taken from the X-rays are transferred to the actual bone at surgery. Bony landmarks are needed for either traditional plastic overlays or software-based systems. Exact localization of the bony landmarks which appear on the X-rays in two dimensions may be difficult to replicate in the three-dimensional reality of the patient's anatomy. Rotation of measuring instruments about curved surfaces or past soft tissues overlying the bony landmarks can render these known techniques unreliable. Any of these errors can result in unwanted complications, such as femoral neck failure due to malpositioning of the reference pin causing a misaligned jig and a resulting erroneously installed prosthesis.

SUMMARY OF THE INVENTION

In an embodiment of the present invention, a method for planning the implantation of a prosthetic joint component in a prosthesis-receiving bone is described. Surrounding soft tissue is retracted to expose the prosthesis-receiving bone. A prosthetic joint component planning template comprising a planar template body having a unitary structure is provided. The planning template is positioned in a superimposed orientation with a curvilinear surface of an exposed prosthesis-receiving bone. The position of the planning template is adjusted into a desired superimposed orientation with respect to the prosthesis-receiving bone. At least one of a size and an orientation of the prosthetic joint component is determined through visualization of the planning template and the prosthesis-receiving bone.

In an embodiment of the present invention, a prosthetic joint component planning template for assisting a user with determining at least one of a size and an orientation of a prosthetic joint component is described. The planning template comprises a planar template body having a unitary structure. The planning template is adapted for positioning in a superimposed orientation with a curvilinear surface of an exposed prosthesis-receiving bone to assist a user with visualizing the prosthetic joint component in an implanted position.

In an embodiment of the present invention, a system for planning the implantation of a joint prosthesis component is described. The system comprises a plurality of prosthetic joint component planning templates. Each planning template comprises a planar template body having a unitary structure. At least one of the plurality of planning templates is selectable by a user for positioning in a superimposed orientation with a curvilinear surface of an exposed prosthesis-receiving bone to assist the user with visualizing the prosthetic joint component in an implanted position.

BRIEF DESCRIPTION OF THE DRAWINGS

For a better understanding of the invention, reference may be made to the accompanying drawings, in which:

FIG. 2 is a side view, taken along line 2-2 in FIG. 1, of an example configuration of the embodiment of FIG. 1;

FIG. 3 is a top view, taken along line 3-3 in FIG. 2, of an example configuration of the embodiment of FIG. 1;

FIG. 4 is a front view, similar to FIG. 1, of an example configuration of the embodiment of FIG. 1 for a first surgical procedure;

DESCRIPTION OF EMBODIMENTS

Figure 1:
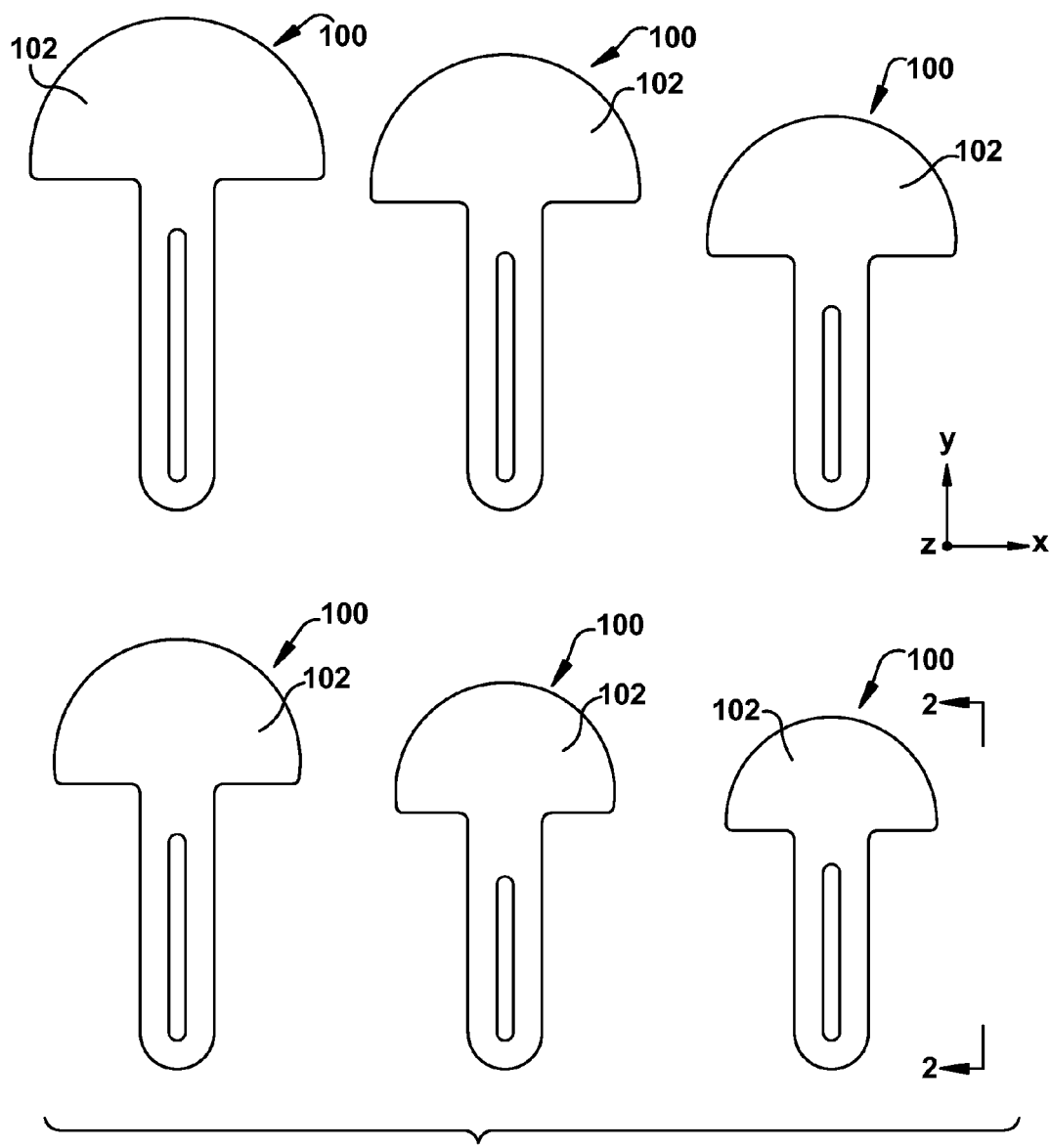
FIG. 1 is a front view of an embodiment of the present invention, illustrating multiple configurations thereof.

In accordance with the present invention, FIG. 1 depicts a group of prosthetic joint component planning templates 100 according to an embodiment of the present invention. The multiple planning templates 100 shown in FIG. 1 illustrate multiple configurations of possible planning templates, in which the templates are substantially scaled versions of a single template shape. However, differences in size, orientation, proportions, shape, and/or other physical properties among a group of planning templates 100 for a particular use environment are contemplated. The planning templates 100 of FIG. 1 are intended for use in a hip replacement or resurfacing procedure and will be discussed as such below. One of ordinary skill in the art, though, could readily provide one or more planning templates 100, having any suitable similar or assorted physical properties, for any prosthetic joint component to be implanted into a patient.

The planning templates 100 each include a planar template body 102 having a unitary structure. "Planar" is used here to indicate a structure lying in a plane and two-dimensional in quality; a "planar" template body 102 has a two-dimensional outline or border 104 but may be substantially of a constant thickness in the third dimension. For example, and as can be seen by comparing FIGS. 1, 2, and 3, the planning template 100 has a variable profile in the X and Y directions but is planar because the Z-direction profile is constant. It is contemplated that one or more small anchoring pins or spikes (not shown) may project from the planning template 100 to help steady and maintain the planning template in a desired orientation, but these spikes, when present, will not destroy the generally planar nature of the planning template. While the template body 102 is planar, the material forming the planning template 100 is optionally somewhat flexible, for advantages in physical durability and/or ease of visualization.

"Unitary" is used herein to indicate that each planning template 100 is an undivided whole, with no moving parts or separable sections. The template body 102 may be integrally formed in a unitary manner, such as from a single piece of template material. Alternately, the template body 102 may be made up of one or more subassemblies (not shown), attached together, in any suitable manner, into a final unitary whole. At least a portion of the template body 102 may be at least one of transparent and translucent, to facilitate visualization therethrough by the user. For example, the template body 102 may be at least partially made of a mesh or Plexiglas® material. It is also contemplated that the template body 102 may be marked in some manner to assist the user in the visualization process. For example, size and/or orientation markings could be printed or etched onto a surface of the template body 102.

Each planning template 100 can assist a user with determining at least one of a size and an orientation of a prosthetic joint component. Accordingly, the planning template 100 should reflect the dimensions of the prosthetic joint component. Turning to FIG. 4, a femoral prosthetic hip component 404 for a first surgical procedure is shown. The femoral prosthetic hip component 404 here is a cup-shaped prosthesis used in a hip resurfacing procedure. The template body 102 is bounded by a template outline 406. The template outline 406 is at least partially chosen to approximate a projected silhouette of at least a portion of the prosthetic joint component. The term "projected silhouette" is used herein to indicate the outline of a body viewed as circumscribing a mass, and may be described in more detail as the shape of the shadow thrown upon a flat surface by a prosthetic joint component placed in a desired orientation with respect to the flat surface and then illuminated from a side opposite the flat surface. The term "approximate" is used herein to indicate that the planning template has characteristics that come near to those of the prosthetic joint component; the planning template 100 does not necessarily precisely replicate the projected silhouette due to particular manufacturer and/or user considerations or preferences. For example, if the projected silhouette includes a narrow protrusion, the planning template 100 may be wider in that area for durability, particularly when the width of that portion of the planning template 100 is not crucial to surgical planning.

As shown in FIG. 4, the planning template 100 of the Figures includes a template outline 406 defining a dome-shaped head portion 408 with an elongate shaft portion 410 extending therefrom to approximate a projected silhouette of the femoral prosthetic hip component 404. The projection itself is indicated schematically by the dashed lines of FIG. 4. Obviously, the template outline 406 should approximate a prosthetic joint component silhouette which is projected in an orientation substantially similar to that in which the prosthetic joint component will be oriented in the prosthesis-receiving bone. In this "projection orientation" respect, the planning template 100 is generated similarly to the known 115% overlay template currently used with an X-ray for preoperative planning.

The template body 102 may include at least one pin insertion aperture 412. The pin insertion aperture 412 extends through the template body 102, as shown in phantom line in FIGS. 2 and 3, and is configured to allow the passage through the template body 102 of a reference pin (not shown). The pin insertion aperture, shown at 412 as an elongate slot, may have any desired size, cross-sectional shape(s), orientation, location on the template body 102, or any other physical characteristics. For example, a line or other grouping of a plurality of circular pin insertion apertures (not shown) could provide the user with a more defined guidance of the reference pin through the template body 102. As another example, one or more pin insertion apertures 412 could extend through the template body 102 at an angle to the X-Y plane defined by the planning template 100, to help the user with angling the reference pin in a desired manner. Because the installed reference pin is used as an orientation aid for later portions of the surgical procedure (as discussed in the Background section, above), the pin insertion aperture(s) 412 should be located in an area of the template body 102 which reflects the user's likely desired placement of a reference pin with respect to the prosthesis-receiving bone. The portion of the planning template 100 in which the pin insertion aperture 412 is located may deviate from the precise projected silhouette of the prosthetic joint component in order to accommodate the pin insertion aperture.

Figure 5:
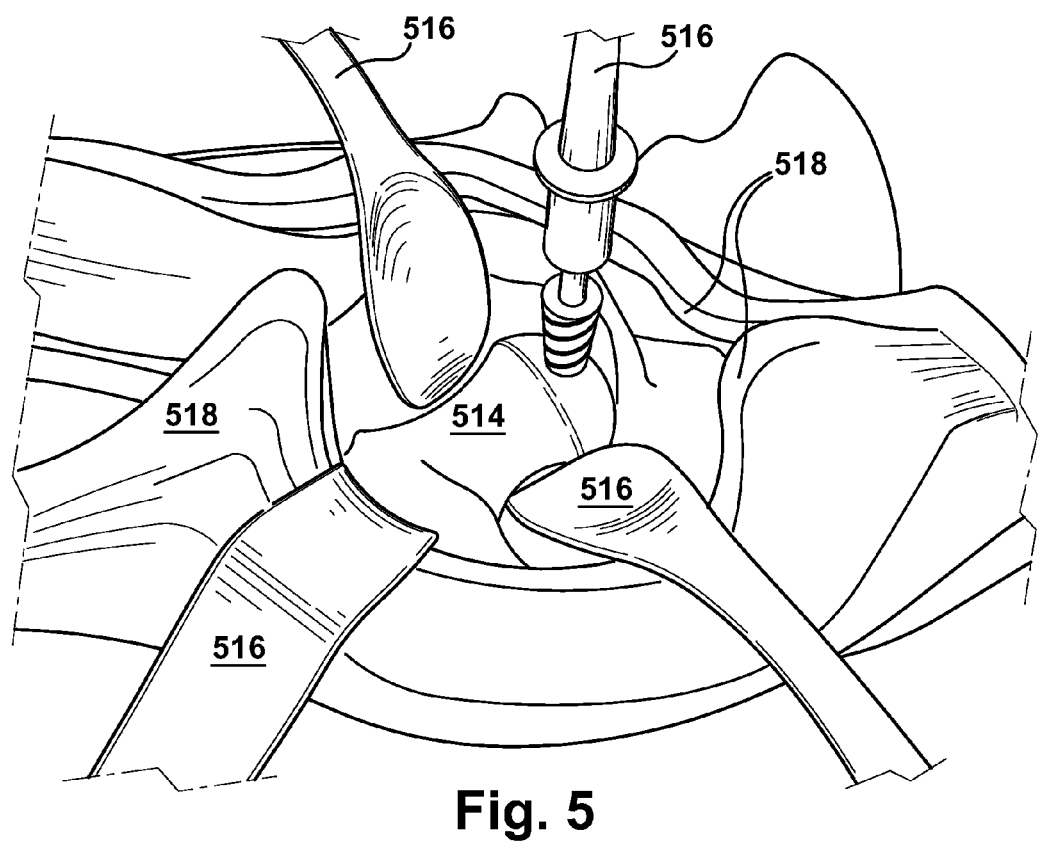
FIG. 5 depicts an example use environment for the embodiment of FIG. 1.

FIG. 5 depicts an example use environment for the planning template 100. In FIG. 5, a femur has been exposed for a hip resurfacing operation, though the initial stages of many hip procedures will result in a similarly appearing example use environment. The upper thigh and hip area are shown here, with an incision allowing access to the upper femur 514. Surgical manipulation tools 516, such as retractors, have been used to move and hold the patient's muscles, joint capsule, and other soft tissues 518 away from the surgical site, thus exposing the upper femur 514 to view and access from outside the patient's body. In this example, the upper femur 514 is the prosthesis-receiving bone. However, in other use environments, the prosthesis-receiving bone of interest may be at least one of a femur, a pelvis, a tibia, a fibula, a scapula, a humerus, a radius, an ulna, a tarsal bone, a metatarsal bone, a carpal bone, a metacarpal bone, a spinal bone, an ankle region bone, and a wrist region bone.

As shown in FIG. 5, the upper femur 514 has been dislocated from the remaining portions of the hip joint (not shown) and been oriented into a position that corresponds with the orientation of the projected silhouette of the femoral prosthetic hip component 404 (as represented by the planning template 100). The exposed portion of the upper femur 514 naturally has a native (i.e., not altered) bone surface which is curvilinear (i.e., extends three-dimensionally into and out of the plane of the page of FIG. 5). The native bone surface may be left unaltered, or may instead be cut, ground, drilled, milled, rasped, or otherwise modified as desired, which may occur during a resurfacing procedure. However, when the surgery is intended to replace the upper femur 514, there should be no need for mechanical alteration of the upper femur before it is removed from the patient.

At the stage of surgery shown in FIG. 5, a user may choose to employ a system for planning the implantation of a joint prosthesis component in a prosthesis-receiving bone, according to the present invention. In such a system, the user is provided with a plurality of assorted planning templates 100, such as the multiple configurations shown in FIG. 1. Each of the plurality of planning templates 100 may have at least one dimension correlated with at least one dimension of a prosthetic joint component from a range of available prosthetic joint components which can each be implanted into the patient. For example, the plurality of planning templates 100 could each have the same template outline 406 at different scales to correlate with differently sized prosthetic joint components having the same configuration.

Alternately, the plurality of planning templates 100 could each evince a differently shaped and/or proportioned template outline 406 to correlate with differently configured prosthetic joint components, which may also be of different sizes. In any event, though, it is contemplated that each of the plurality of planning templates 100 of the system has at least one dimensional difference from at least one other planning template, in order to provide the user with a variety of planning templates to suit a particular joint replacement application.

Figure 6:
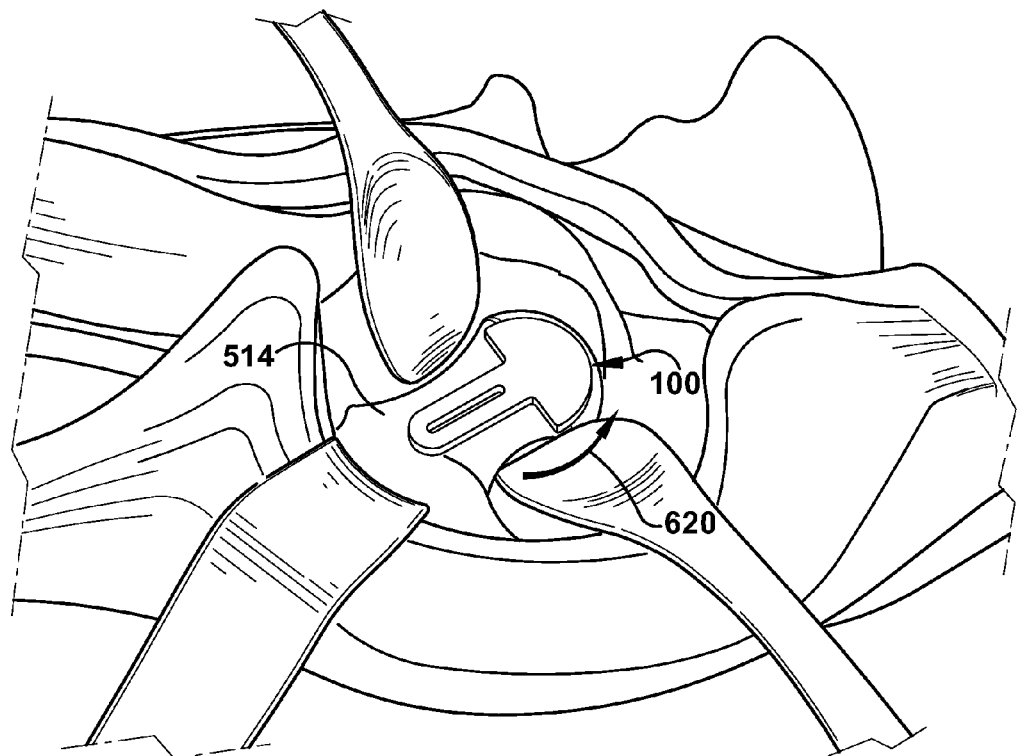
FIGS. 6-7 depict a sequence of operation of the embodiment of FIG. 1 in the example use environment of FIG. 5.

In order to use the system, the user selects a planning template 100 and places the planning template in a superimposed orientation with a curvilinear surface of the exposed prosthesis-receiving bone. The term "superimposed" is used herein to indicate that the planning template 100 is placed or laid over or above the prosthesis-receiving bone, as seen from the point of view of the user. In a "superimposed" position, the planning template 100 appears to be co-located with the prosthesis-receiving bone, as shown in FIG. 6. When the planning template 100 is at least partially transparent or translucent, the user may be able to view at least a portion of the upper femur 514 through the template body 102. Alternately, an opaque planning template will obscure the superimposed portions of the prosthesis-receiving bone, which may be desirable in some applications of the present invention.

The planning template 100 may be adapted for noninvasive positioning in the superimposed orientation with the curvilinear surface of the exposed prosthesis-receiving bone. The term "noninvasive" is used herein to indicate that the planning template 100 does not infiltrate or enter the patient's body through the surgical wound, and does not become superposed between two or more body tissues. In contrast, a user may position the planning template 100 in an invasive manner, such as between two bones, between a soft tissue and a bone, and/or otherwise at least partially within an intrabody or intra joint space.

Figure 7:
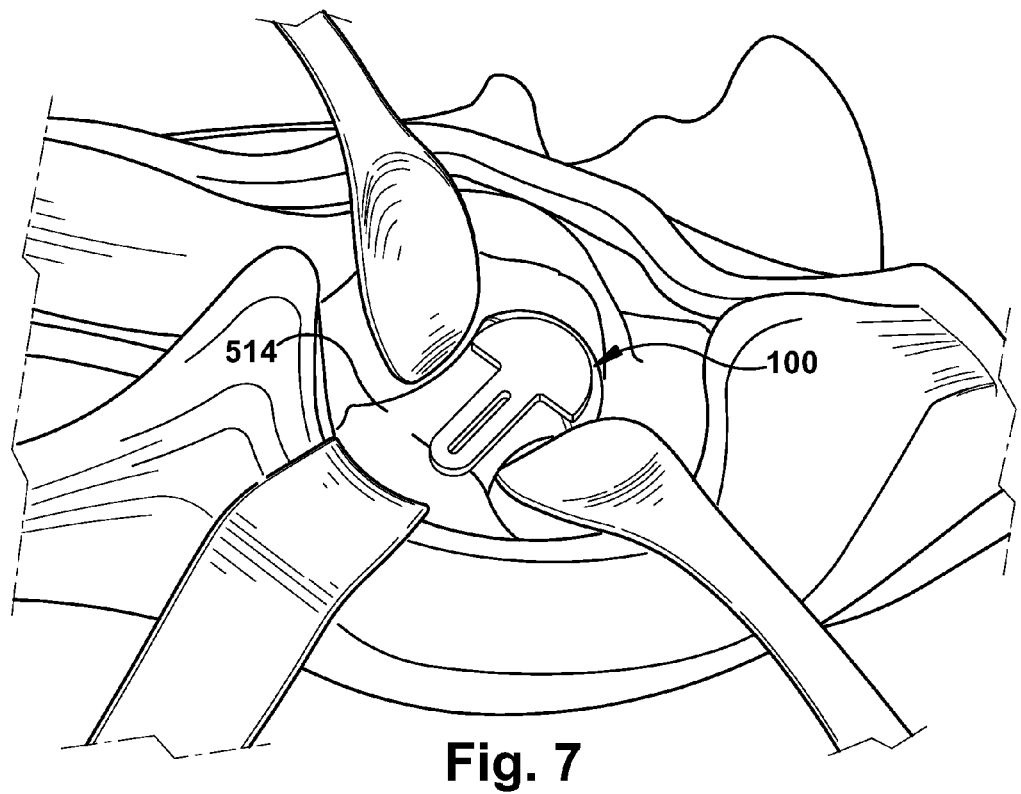

Returning to the sequence of FIGS. 6 and 7, once the planning template 100 has been placed into the superimposed orientation with the curvilinear surface of the exposed prosthesis-receiving bone, the user may adjust the position of the planning template with respect to the prosthesis-receiving bone. For example, when the prosthesis-receiving bone is an upper femur 514, the user may initially place the planning template 100 adjacent a head and neck of the upper femur in an orientation mimicking that of the native upper femur, as shown in FIG. 6. The term "adjacent" here is used to indicate that the planning template 100 is in a position near, and optionally touching, the upper femur 514. This adjacent placement assists the user in accurately visualizing the planning template 100 near the upper femur 514.

It has been shown that a slight valgus placement, where the femoral prosthetic hip component 404 is somewhat more vertical than the patient's own anatomy, provides favorable results for the hip resurfacing surgery. Thus, once the planning template 100 is in the native upper femur orientation adjacent the head and neck of the upper femur 514, the user may tilt the planning template in the tilt direction (shown in FIG. 6 by arrow 620) and into a desired valgus position corresponding to an orientation of implantation, with this adjusted position hereafter referenced as a "final template position". The planning template 100 may be only slightly tilted in the final template position, or may be substantially tilted and/or shifted from the initial native upper femur orientation, as desired by the user. The tilt angle(s) shown in the Figures are for example purposes only, and one of ordinary skill in the art can readily provide a desired amount of tilting, in any direction or orientation, for a particular application of the present invention. The planning template 100 may be tilted only within the X-Y plane or may be tilted three-dimensionally, if desired. It is presumed, though, that most user will prefer to keep the X-Y plane of the planning template 100 substantially perpendicular to the user's view direction, in order to avoid introducing distortion to the user's visualization of the planning template in relation to the upper femur 514.

Alternately, and after the chosen planning template 100 has been placed in the native upper femur orientation adjacent the head and neck of the upper femur 514, the user may evaluate the chosen planning template with respect to the upper femur and responsively select an other of the plurality of planning templates (when provided) for positioning in the superimposed orientation with the upper femur. This could be done, for example, when the user decides that the chosen planning template 100 is the wrong size for that particular patient and the other planning template 100 is a more appropriate size. This process may be repeated as often as desired until the user is satisfied that the correct planning template 100 is being used. Since each planning template 100 corresponds to a different size and/or configuration of a prosthetic joint component, the user thus can select a prosthetic joint component for implantation responsive to the visualization of the planning template superimposed over the prosthesis-receiving bone.

Once the user is satisfied with the choice of planning template 100 being used, the planning template may be moved in the tilt direction 620 into the final template position, as previously described. While the planning template 100 is useful in simulating a projection of a particular prosthetic joint component onto the prosthetic-receiving bone, the user determines the desired final template position based at least partially upon known principles of prosthetic implantation and the user's own knowledge and experience. Therefore, the planning template 100 assists the user with visualizing the prosthetic joint component in an implanted position without being subject to the magnification and two-dimensional/three-dimensional conversion problems of the currently used X-ray overlay technique. Accordingly, the user may determine at least one of the size and the orientation of the desired prosthetic joint component through visualization of the planning template 100 and the prosthetic-receiving bone. In this manner, the planning template 100 assists the user with quickly and accurately selecting a desired prosthetic joint component for implantation into a patient from among an available universe of candidate prosthetic joint components.

Optionally, and once a planning template 100 of the desired size and configuration has been placed into the final template position, the planning template may be used to help place a reference pin into position to assist with remaining portions of the joint resurfacing or replacement surgery. A reference pin (not shown) of any suitable type is provided; the reference pin here will be described as being associable with a pin hole (not shown) previously drilled in a prosthesis-receiving bone.

The pin insertion aperture 412 of the planning template, when provided, could assist with placement of the reference pin.

When the planning template 100 is in the final template position, the planning template may be in contact with the prosthesis-receiving bone. The term "contact" is used herein to indicate a touching connection; "contact" between two or more structures can include a surface, and/or a penetrating, associative relationship. Whether or not contact is made between the planning template 100 and the prosthesis-receiving bone, however, the pin insertion aperture 412 may be used to guide the reference pin into contact with the prosthesis-receiving bone.

One way in which the reference pin may be guided by the pin insertion aperture 412 is that at least a portion of a drill bit (not shown) may be placed within the pin insertion aperture. The drill bit could then be actuated to drill a pin hole into the prosthesis-receiving bone, with the drill bit optionally being guided in orientation and/or position by the pin insertion aperture 412. The drill bit size and type should be chosen for efficacy in forming an appropriately sized and placed pin hole as desired by the user, with consideration of factors such as, but not limited to, reference pin material, reference pin size, reference pin configuration, desired pin hole depth, physical properties of the prosthesis-receiving bone, and the like.

Whether or not a pin hole is drilled, at least a portion of the reference pin may pass through the pin insertion aperture 412 and be placed in contact with the prosthesis-receiving bone. After the reference pin has been inserted into the pin hole and is stably held in the desired relationship with the prosthesis-receiving bone, the planning template 100 may be removed from the final template position, such as by being lifted away from the prosthesis-receiving bone. Thus, the reference pin will pass completely through the pin insertion aperture 412 as the planning template 100 is removed from the surgical area. Alternately, the planning template 100 may be removed from the surgical area once a pin hole has been formed in the prosthesis-receiving bone, thus allowing the reference pin to be placed directly into the pin hole without passing through the planning template 100. This may be desirable if, for example, at least a portion of the reference pin has a larger cross-sectional area than the pin insertion aperture 412.

Regardless of the way in which the planning template 100 and reference pin are employed, at this stage of the surgical procedure, the reference pin will have been placed in a desired location and orientation with respect to the prosthesis-receiving bone. The user may then proceed with the joint resurfacing or replacement surgery, secure in the knowledge that the reference pin has been reliably placed and provides a stable and desirable point of reference, such as for the anchoring of a jig (not shown) which can be used throughout the remainder of the surgical procedure.

While aspects of the present invention have been particularly shown and described with reference to the preferred embodiment above, it will be understood by those of ordinary skill in the art that various additional embodiments may be contemplated without departing from the spirit and scope of the present invention. For example, the template outline 406 may be selectively magnified or minimized from the actual dimensions of the corresponding prosthetic joint component, to provide the user with a safety or confidence factor/cushion in the visualization process. The planning template 100 could be made of any suitable material or combination thereof. A pin hole could be formed in the prosthesis-receiving bone without use of the pin insertion aperture 412, regardless of whether the reference pin passes through the pin insertion aperture. The pin insertion aperture 412 could be contiguous with the template outline 406 to allow the planning template 100 to be laterally removed from around the inserted reference pin. A jig, block, or stop (not shown) could be provided to help control a drilled depth of the pin hole. A handle (not shown) or other manipulation aid could be provided as part of, or in addition to, the planning template, even if the handle does not approximate the projected silhouette of the joint prosthesis component. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. A method for planning the implantation of a prosthetic joint component in a prosthesis-receiving bone, the method comprising the steps of:
    retracting surrounding soft tissue to expose the prosthesis-receiving bone, the prosthesis-receiving bone being a femur;
    providing a unitary prosthetic joint component planning template consisting of a planar template body having a unitary structure which is an undivided monolithic whole;
    positioning the unitary planning template in a superimposed orientation with a curvilinear surface of an exposed prosthesis-receiving bone;
    adjusting the position of the unitary planning template into a desired superimposed orientation with respect to the prosthesis-receiving bone, including
        placing the unitary planning template adjacent a head and a neck of the femur in an orientation mimicking that of a native femur; and
        tilting the unitary planning template into a desired valgus position; and
    determining at least one of a size and an orientation of the prosthetic joint component through visualization of the unitary planning template in the desired superimposed orientation with respect to the prosthesis-receiving bone.

2. The method of claim 1, including the steps of:
    providing at least one pin insertion aperture extending through the template body;
    providing at least one reference pin;
    passing at least a portion of the reference pin through the pin insertion aperture; and
    placing at least a portion of the reference pin in contact with the prosthesis-receiving bone.

3. The method of claim 2, including the steps of:
    placing at least a portion of a drill bit within the pin insertion aperture;
    drilling a pin hole into the prosthesis-receiving bone with the drill bit; and
    inserting the reference pin into the pin hole.

4. The method of claim 1, wherein the step of adjusting the position of the unitary planning template into a desired superimposed orientation with respect to the prosthesis-receiving bone includes the step of viewing at least a portion of the prosthesis-receiving bone through the template body.

5. The method of claim 1, including the steps of:
    providing a plurality of unitary planning templates, with each of the unitary planning templates having at least one dimensional difference from at least one other unitary planning template; and
    selecting a chosen one of the plurality of unitary planning templates for positioning in the superimposed orientation with the prosthesis-receiving bone.

6. The method of claim 5, including the steps of:
evaluating the chosen unitary planning template with respect to the prosthesis-receiving bone; and
selecting another one of the plurality of unitary planning templates for positioning in the superimposed orientation with the prosthesis-receiving bone responsive to the evaluation of the chosen unitary planning template.

7. The method of claim 1, wherein the step of determining at least one of a size and an orientation of the prosthetic joint component through visualization of the unitary planning template in the desired superimposed orientation with respect to the prosthesis receiving bone includes the steps of:
correlating at least one dimension of the unitary planning template with at least one dimension of the prosthetic joint component; and
selecting a prosthetic joint component for implantation from a range of available prosthetic joint components responsive to the visualization of the unitary planning template in the desired superimposed orientation with respect to the prosthesis-receiving bone.

8. The method of claim 1, wherein the step of determining at least one of a size and an orientation of the prosthetic joint component through visualization of the unitary planning template includes the step of determining both of the size and the orientation of the prosthetic joint component through visualization of the unitary planning template in the desired superimposed orientation with respect to the prosthesis-receiving bone.

9. The method of claim 1, wherein the step of determining at least one of a size and an orientation of the prosthetic joint component through visualization of the unitary planning template includes the step of placing the unitary planning template in the desired superimposed orientation directly adjacent to the prosthesis-receiving bone during a surgical procedure.

10. The method of claim 9, wherein the step of determining at least one of a size and an orientation of the prosthetic joint component through visualization of the unitary planning template includes the step of determining both of the size and the orientation of the prosthetic joint component through visualization of the unitary planning template in the desired superimposed orientation with respect to the prosthesis-receiving bone.

* * * * *